(12) United States Patent
Davenport

(10) Patent No.: US 7,781,163 B2
(45) Date of Patent: Aug. 24, 2010

(54) G-QUADRUPLEX BINDING ASSAYS AND COMPOUNDS THEREFOR

(76) Inventor: Lesley Davenport, 219 Amboy Ave., #9, Metuchen, NJ (US) 08840

( * ) Notice: Subject to any disclaimer, the term of this patent is extended or adjusted under 35 U.S.C. 154(b) by 1198 days.

(21) Appl. No.: 10/754,052

(22) Filed: Jan. 8, 2004

(65) Prior Publication Data

US 2004/0152116 A1 Aug. 5, 2004

Related U.S. Application Data

(60) Provisional application No. 60/439,051, filed on Jan. 8, 2003.

(51) Int. Cl.
C12Q 1/68 (2006.01)
C12M 1/00 (2006.01)
C12M 1/34 (2006.01)
C07H 19/00 (2006.01)
C07H 21/02 (2006.01)

(52) U.S. Cl. ............... 435/6; 435/283.1; 435/287.1; 435/287.2; 536/22.1; 536/23.1

(58) Field of Classification Search .............. 435/6, 435/283.1, 287.1, 287.2; 536/22.1, 23.1
See application file for complete search history.

(56) References Cited

U.S. PATENT DOCUMENTS

| 5,552,540 A | * | 9/1996 | Haralambidis | ........... 536/25.34 |
| 5,612,468 A | | 3/1997 | Hawkins et al. | |
| 5,691,145 A | * | 11/1997 | Pitner et al. | ............... 435/6 |
| 5,849,489 A | * | 12/1998 | Heller | ........................... 435/6 |
| 5,891,639 A | | 4/1999 | Harley et al. | |
| 6,140,480 A | * | 10/2000 | Kool | ........................ 536/18.1 |
| 6,194,206 B1 | | 2/2001 | West et al. | |
| 6,333,155 B1 | * | 12/2001 | Lockhart et al. | ............... 506/9 |

FOREIGN PATENT DOCUMENTS

WO    WO95/31469    11/1995
WO    WO 99/40087   * 8/1999

OTHER PUBLICATIONS

Hawkins, et al. Analytical Biochemistry 1997; 244:86-95.*
Dias et al, J. Am. Chem. Soc., vol. 116, pp. 4479-4480 (1994).*
Mishra et al, Spectrochim. Acta A: Molec. and Biomolec. Spectro., vol. 57, pp. 2433-2450 (Oct. 2001).*
Patel et al, Oxford Handbook of Nucleic Acid Structure, ed. Stephen Neidle, Oxford Science Publications, Chapter 13 (1998).*
The definition of 3MI [retrieved on Aug. 31, 2009]. Retrieved from the Internet: <URL: www.fidelitysystems.com/3MI.html>.*
Gros et al, Nucl. Acids Res., vol. 35, pp. 3064-3075 and Supplemental Material, published online Apr. 20, 2007.*

(Continued)

*Primary Examiner*—Robert T. Crow
(74) *Attorney, Agent, or Firm*—Pepper Hamilton LLP

(57) ABSTRACT

The present invention provides methods for assaying binding of compounds to G-quadruplex structures. Also provided are methods for screening candidate compounds for use as modulators of G-quadruplex activity, and methods for screening candidate compounds for telomerase inhibitory activity. The invention further provides novel compounds useful in the assays of the invention.

20 Claims, 4 Drawing Sheets

OTHER PUBLICATIONS

Myers et al, J. Biol. Chem., vol. 278, pp. 42300-42306, published Aug. 6, 2003.*

Mergny et al., "Telomerase inhibitors based on quadruplex ligands selected by a fluorescence assay," *PNAS* (2001) 98(6)3062-3067.

Sastry "A fluorescence-based assay for transcription using a novel fluorescent GTP analogue," *Biophysical Chemistry* (2001) 91:191-208.

International Search Report dated May 20, 2005 for International Application No. PCT/US04/00389.

Hussein, et al., "Binding of anionic porphyrin molecules to G-guadruplexed DNA using fluorescently labeled guanine-telomeric sequences," Biochem. J. (2003) 84:44a.

Hemann and Greider, "G-strand overhangs on telomeres in telomerase-deficient mouse cells," Nuc. Acids Res. (1999)27:3964-3969.

Riou, et al., "Cell senescence and telomere shortening induced by a new series of specific G-quadruplex DNA ligands," Proc. Natl. Acad. Sci. USA (2002) 99:2672-2077.

Herbert, et al., Inhibition of human telomerase in immortal human cells leads to progressive telomere shortening and cell death, Proc. Natl. Acad. Sci. USA (1999) 98:14276-14281.

Hwang, "Replicative senescence and senescence-like state induced in cancer derived cells," Mach. Ageing Dev. (2002) 123:1681-1694.

Perry and Jenkins, "Recent advances in the development of telomerase inhibitors for the treatment of cancer." Expert Opin. Invest. Drugs (1999) 8:1981-2008.

Simonsson, "G-quadruplex DNA structures: variations on a theme," Biol. Chem. (2001) 382-621-628.

Davis and Siu, "Telomerase: therapeutic potential in cancer," Cancer Invest. (2000) 18:269-277.

Elmore and Holt, "Telomerase and telomerase stability: a new class of tumor suppressor?," Mol. Carcinog. (2000) 28:1-4.

Federoff, et al., NMR-based model of a telomerase-inhibiting compound bound to G-quadruplex DNA. Biochemistry (1998) 37:12367-12374.

Hurley, et al., "G-quadruplex as tarets for drug design," Pharmacol. Ther. (2000) 85:141-155.

Mergny, et al., "Following G-quartet formation by UV-spectroscopy," FEBS lett. (1998) 435:74-78.

Risitano, et al., "Stability of intramolecular DNA quadruplexes: comparison with DNA duplexes," Biochemistry (2003) 42:6507-6513.

Use of pteridine nucleoside analogs as hybridization probes by Mary E. Hawkins and Frank M. Balis, Published online Apr. 16, 2004. Nucleic Acids Research 2004, vol. 32, No. 7 e62.

* cited by examiner

G-QUADRUPLEX BINDING ASSAYS AND COMPOUNDS THEREFOR

CROSS-REFERENCE TO RELATED APPLICATIONS

The present application claims priority benefit of U.S. Provisional Application Ser. No. 60/439,051 filed Jan. 8, 2003, the entire contents of which are incorporated herein by reference.

FIELD OF THE INVENTION

The present invention relates to the field of G-quadruplex structures, and more specifically to methods for assaying the binding of compounds to G-quadruplex structures, methods for screening candidate compounds for use as modulators of G-quadruplex activity. In some embodiments, the invention relates to methods for screening candidate compounds for telomerase modulating (inhibitory or enhancing) activity, to telomerase modulators (e.g., inhibitors and enhancers) identified by the methods, and to therapeutic applications of the compounds identified by the methods.

BACKGROUND OF THE INVENTION

Telomeres are specialized regions of non-coding repeated DNA sequences bound by proteins which form condensed, heterochromatic structures at the ends of chromosomes. During cell division, the process of DNA replication at the ends of chromosomes is imperfect, and a special enzyme known as telomerase is required to replicate telomeric DNA sequences. With each round of replication, telomeres become progressively shorter, and after approximately 50 cell cycles, the shortened telomeres cease to function, leading to cell death; thus, shortening of telomeres is associated with aging. Another indication that telomere function is associated with cellular longevity comes from the observation that 90% of immortalized tumor cells exhibit enhanced telomerase activity (Hwang, *Mech. Ageing Dev.* 123(12):1681-94, 2002; Perry & Jenkins, 1999). In addition to protecting chromosomal ends from "erosion" during replication, telomeres also protect chromosomal ends from degradation by nucleases. Interfering with the process of telomere replication by telomerase and thereby diminishing the protective activity of telomeres may be an effective means of speeding up cellular senescence.

The DNA found within telomeres contains tandem repeats of simple motifs such as $(5'-TTAGGG)_n$ in Homo sapiens and $(5'-TTGGGG)_n$ in the ciliate, *Tetrahymena* (Herbert et al., 1999; Hemann & Greider, 1999), and these DNA sequences are known to adopt an unusual, highly stable structure formed by Hoogsteen base-pairing between guanine residues. These four-stranded guanine-rich DNA molecular structures are known as G-quadruplexes, DNA tetraplexes or G-quartets. G-quadruplexes are believed to be associated with switch recombination during the differentiation of B lymphocytes, as well as being involved in gene regulation and disease states such as cancer and Werner's syndrome (Simonsson, *Biol. Chem.*, 382, 621-628; 2001). G-quadruplexes are stabilized by physiological concentrations of potassium ions, and have been shown to directly inhibit the activity of telomerase, implicated in tumorigenesis (Davies & Siu, 2000; Elmore & Holt, 2000). Thus, compounds which stabilize G-quadruplexes and interfere with telomerase activity may serve useful as antitumor agents by causing telomere instability and combating the uncontrolled cellular proliferation observed in cancer (Riou, *PNAS,* 99(5):2672-2677; 2002).

While inhibition of telomerase activity can be achieved by several approaches, including altering the enzyme's RNA template or interactions with its reverse transcriptase active site, numerous studies have focused on stabilizing the inhibitory G-quadruplex structure formed by the telomeres. Molecules studied for their ability to stabilize G-quadruplex structures include the classic DNA intercalators ethidium and amido-anthraquinones. These molecules appear to drive the single-strand telomere-quadruplex equilibrium in favor of the folded quadruplex complex. In contrast, perylene derivatives and tetra-(N-methyl-pyridyl)-porphyrin appear to stack on the exterior of the quadruplex. In addition, it has been reported that a series of porphyrin derivatives demonstrate selectivity between three possible G-quadruplex types. Thus, identifying and characterizing the stability of the ligand-G-quadruplex complex remains a challenge. In addition, all so-called G-quadruplex promoters thus far reported demonstrate some affinity for duplex-DNA and tend to exhibit cytotoxicity in addition to the desirable telomerase inhibitory properties.

Given the link between G-quadruplex stabilization and inhibition of telomerase, and their presumed utility as a means of triggering senescence, it is clear that molecules that G-quadruplex stabilizers are of great potential benefit as therapeutics. To date, however, the search for such molecules has been hampered by the lack of a facile assay of G-quadruplex binding. For example, previous assays for monitoring binding of molecules to quadruplex-DNA have involved titration-NMR methodologies (Fedoroff et al., 1998; Hurley et al., 2000), relatively insensitive UV spectroscopy (Mergny et al., 1998), and time-consuming DNA-polymerase stop-assays (Han et al., 1999). While the NMR approach provides detailed structural information, the large and expensive equipment required does not lend itself to rapid screening of many potential quadruplex-binding molecules. Alternatively, an elegant time-resolved fluorescence assay using $Eu^{3+}$ long-lived fluorophores bound to telomeric fragments (Bare et al., 1998), targets telomerase activity rather than quadruplex-DNA binding, and involves time-consuming PCR amplification.

Consequently, there remains a long felt need for a rapid and facile micro-method for assaying the binding of molecules to G-quadruplex DNA, and methods which facilitate the screening a library of molecules for their ability to bind and stabilize G-quadruplex structures, toward the discovery of potential therapeutics. It is clear that such a rapid and facile micro-method for assaying the binding of molecules to G-quadruplex DNA, and methods for screening molecules for their ability to stabilize the G-quadruples structure would be of great benefit in the discovery of potential therapeutics. This invention is directed to these, as well as other, important ends.

SUMMARY OF THE INVENTION

In some embodiments, the present invention provides methods for determining the binding affinity of a candidate compound for G-quadruplex structures comprising the steps of:

(a) providing a G-quadruplex analog, said analog having at least one intrinsic fluorescent moiety;

(b) contacting said G-quadruplex analog with a candidate compound; and (c) measuring a difference in a fluorescence property of said G-quadruplex analog.

In some embodiments, at least one fluorescent moiety of said G-quadruplex analog is a fluorescent nucleobase analog. In further embodiments, each of said fluorescent moieties of said G-quadruplex analog is a fluorescent nucleobase analog. In other embodiments, said G-quadruplex analog contains one or more fluorescent nucleobase analogs. In some embodiments, the G-quadruplex analog contains one, two, three, four, five or six fluorescent nucleobase analogs.

In some embodiments, said G-quadruplex analog comprises a nucleobase sequence that is substantially identical to a human telomeric repeat sequence.

In some embodiments, the nucleobase sequence of said G-quadruplex analog is substantially identical to a human telomeric repeat sequence.

The present invention further provides methods for determining the binding affinity of a candidate compound for G-quadruplex structures comprising the steps of:

(a) providing a G-quadruplex analog having at least one intrinsic fluorescent moiety;

(b) contacting said G-quadruplex analog with a candidate compound; and (c) measuring a difference in a fluorescence property of said G-quadruplex analog;

wherein said G-quadruplex analog has the general structure 5'-TTAGGG (SEQ ID NO: 1), 5'-TTAGGGTTAGGG (SEQ ID NO: 2), 5'-TTAGGGTTAGGGGTTAGGG (SEQ ID NO: 3), 5'-TTAGGGTTAGGGTTAGGGGTTAGGG (SEQ ID NO: 4), 5'-TTAGGGTTAGGGTTAGGGTTAGGGTTAGGG (SEQ ID NO: 5), 5'-TTAGGGTTAGGGTTAGGGT-TAGGGTTAGGGTTAGGG (SEQ ID NO: 6), 5'-TTAGGGT-TAGGGTTAGGGTTAGGGTTAGGGTTAGGGTTAGGG (SEQ ID NO: 7), 5'-TTAGGGTTAGGGTTAGGGT-TAGGGTTAGGGTTAGGGTTAGGGTTAGGG (SEQ ID NO: 8), 5'-ATTGGG (SEQ ID NO: 9), 5'-ATTGGGATTGGG (SEQ ID NO: 10), 5'-ATTGGGATTGGGATTGGG (SEQ ID NO: 11), 5'-ATTGGGATTGGGATTGGGATTGGG (SEQ ID NO: 12), 5'-ATTGGGATTGGGATTGGGATTGGGAT-TGGG (SEQ ID NO: 13), 5'-ATTGGGATTGGGATTGG-GATTGGGATTGGGATTGGG (SEQ ID NO: 14), 5'-AT-TGGGATTGGGATTGGGATTGGGATTGGGATTGGGAT TGGG (SEQ ID NO: 15), or 5'-ATTGGGATTGGGATTGG-GATTGGGATTGGGATTGGGATTGGGATTGGG (SEQ ID NO: 16), wherein at least one of said nucleobases of each of said SEQ ID NOs: 1-16 has been replaced with a fluorescent nucleobase analog.

In some embodiments, the G-quadruplex analog has the structure of any of SEQ ID NOs: 1-8, and one or more guanine bases of positions G5 and G11 have been replaced with a fluorescent nucleobase analog. In further embodiments, the G-quadruplex analog has the structure of any of SEQ ID NOs: 1-8 and the guanine base of position G5 has been replaced with a fluorescent nucleobase analog. In further embodiments, the G-quadruplex analog has the structure of any of SEQ ID NOs: 1-8 and the guanine base of position G11 has been replaced with a fluorescent nucleobase analog. In still further embodiments, the G-quadruplex analog has the structure of SEQ ID NOs: 1-8 and the guanine bases of positions G5 and G11 have been replaced with a fluorescent nucleobase analog.

In some embodiments, the present invention provides methods for determining the binding affinity of a plurality of candidate compounds for G-quadruplex structures comprising the steps of:

(a) providing an array comprising a plurality of sites to which G-quadruplex analogs have been bound, each of said G-quadruplex analogs having at least one intrinsic fluorescent moiety;

(b) contacting said G-quadruplex analogs with a plurality of candidate compound; and (c) measuring a difference in a fluorescence property of one or more of said G-quadruplex analogs.

In some embodiments, the G-quadruplex analogs have the structure of any of SEQ ID NOs: 2-8 or SEQ ID NOs: 9-16, and wherein at least one of said nucleobases of said SEQ ID NOs: 2-8 or SEQ ID NOs: 9-16 has been replaced with a fluorescent nucleobase analog. In further embodiments, the G-quadruplex analogs have the general structure of any of SEQ ID NOs: 2-6 or SEQ ID NOs: 10-14; or SEQ ID NOs: 3-5 or SEQ ID NO: 11-13; or SEQ ID NO: 4 or SEQ ID NO: 12.

In some embodiments, the G-quadruplex analogs have the structure of any of SEQ ID NOs: 9-16 and one or more guanine bases of positions G5 and G11 have been replaced with a fluorescent nucleobase analog; or the guanine base of position G5 has been replaced with a fluorescent nucleobase analog; or the guanine base of position G11 has been replaced with a fluorescent nucleobase analog; or the guanine bases of positions G5 and G11 have been replaced with a fluorescent nucleobase analog.

In some embodiments, the present invention provides G-quadruplex analog polynucleotides having the structure:

$$(5'-(L_1)_q(L_2)_r(L_3)_s(L_4)_t(L_5)_u(L_6)_v)_x$$

wherein:

each $L_1$, $L_2$, $L_3$, $L_4$, $L_5$ and $L_6$ is independently selected from the group consisting of a nucleotide, a nucleotide analog, and a nucleotide comprising a fluorescent nucleobase analog;

q, r, s, t, u and v are each independently 0, 1 or 2, provided that the sum of q+r+s+t+u+v is at least 3; and x is 1 to 8;

provided that:

said sequence 5'-$(L_1)_q(L_2)_r(L_3)_s(L_4)_t(L_5)_u(L_6)_v$ is an analog of a telomeric repeat sequence;

said polynucleotide contains at least one nucleotide comprising a fluorescent nucleobase analog; and said polynucleotide is a G-quadruplex analog.

In some embodiments, the sequence 5'-$(L_1)_q(L_2)_r(L_3)_s(L_4)_t(L_5)_u(L_6)_v$ is an analog of a human telomeric repeat sequence. In further embodiments, q, r, s, t, u and v are each 1. In further embodiments, x is from 2 to 6; or 3 to 5; or x is 4.

In some embodiments, q, r, s, t, u and v are each 1, and x is 4. In some such embodiments, the polynucleotide contains one, two three four, five of six fluorescent nucleobase analogs In further embodiments, the present invention provides compounds having the structure of any of SEQ ID NOs: 2-8 or SEQ ID NOs: 9-16, and wherein at least one of said nucleobases of said sequence SEQ ID NOs: 2-8 or SEQ ID NOs: 9-16 has been replaced with a fluorescent nucleobase analog. In some such embodiments, the G-quadruplex analogs have the general structure of any of SEQ ID NOs: 2-6 or SEQ ID NOs: 10-14; or SEQ ID NOs: 3-5 or SEQ ID NOs: 11-13; or SEQ ID NO: 4 or SEQ ID NO: 12. In further such embodiments, one or more guanine bases of positions G5 and G11 have been replaced with a fluorescent nucleobase analog. In further such embodiments, the guanine base of position G5 has been replaced with a fluorescent nucleobase analog; or the guanine base of position G11 has been replaced with a fluorescent nucleobase analog; or the guanine bases of positions G5 and G11 have been replaced with a fluorescent nucleobase analog.

In some embodiments of the invention, the array is a multiwell plate or a gene chip. In further embodiments, the array comprises beads, is on a column or other solution-based solid support matrix.

In some embodiments of the methods of the invention, the fluorescence property that is measured is selected from the emission wavelength, excitation wavelength, fluorescence intensity, fluorescence lifetime, fluorescence resonance energy transfer (FRET) or fluorescence anisotropy of the fluorescent moiety.

In further embodiments, the present invention provides methods for identifying a candidate compound as a telomerase inhibitor comprising the steps of:
(a) providing a G-quadruplex analog, said analog having at least one intrinsic fluorescent moiety;
(b) contacting said G-quadruplex analog with said candidate compound; and
(c) measuring a difference in a fluorescence property of said G-quadruplex analog upon binding of said compound to said analog. In some embodiments, the compound displaying the difference in step (c) is confirmed to be an inhibitor of telomerase, for example by any of the telomerase assays known in the art.

In some embodiments, the G-quadruplex analogs have the structure of any of SEQ ID NOs: 2-8 or SEQ ID NOs: 9-16, and wherein at least one of said nucleobases of said SEQ ID NOs: 2-8 or SEQ ID NOs: 9-16 has been replaced with a fluorescent nucleobase analog. In further embodiments, the G-quadruplex analogs have the general structure of any of SEQ ID NOs: 2-6 or SEQ ID NOs: 10-14;.or SEQ ID NOs: 11-13; or SEQ ID NO: 4 or SEQ ID NO: 12.

In some embodiments, the G-quadruplex analogs have the structure of any of SEQ ID NOs: 9-16 and one or more guanine bases of positions G5 and G11 have been replaced with a fluorescent nucleobase analog; or the guanine base of position G5 has been replaced with a fluorescent nucleobase analog; or the guanine base of position G11 has been replaced with a fluorescent nucleobase analog; or the guanine bases of positions G5 and G11 have been replaced with a fluorescent nucleobase analog.

In some embodiments of each of the foregoing methods and compounds, the fluorescent nucleobase analog is a pteridine analog, preferably 6-methyl-8-(2-deoxy-β-D-ribofuranosyl) isoxanthopterin.

In some embodiments, the present invention provides a fast and sensitive fluorescence assay for screening potential anticancer drugs that stabilize the G-quadruplexed state of DNA and thus inhibit telomerase activity. Such an intrinsic-fluorescence approach has not previously been employed for studies of quadruplexed DNA structures, and in some embodiments involves the site-specific insertion of one or more fluorescent nucleobase analogs (preferably guanine-analogs) into a human DNA telomeric sequence.

DETAILED DESCRIPTION

Figure 1:
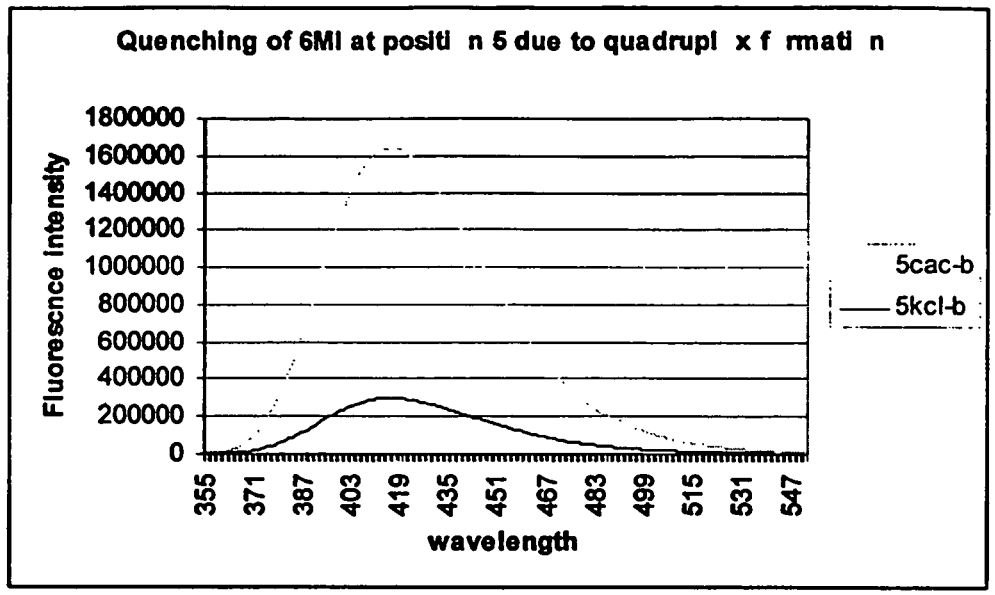
FIG. 1 shows quenching of 6MI at position 5 due to quadruplex formation.
Figure 2:
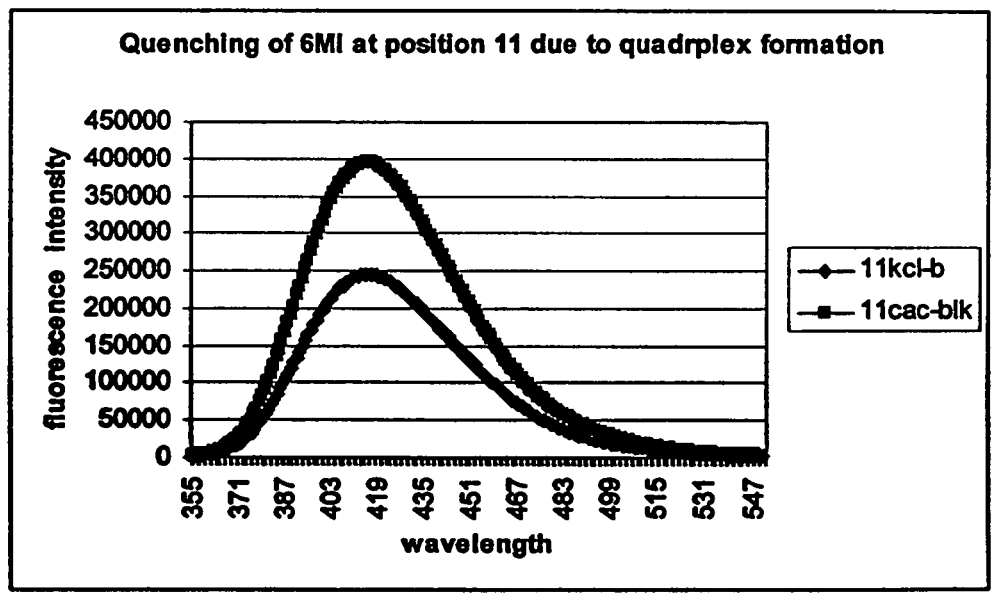
FIG. 2 shows quenching of 6MI at position 11 due to quadruplex formation.

In some embodiments, the present invention provides a model DNA complex which is intrinsically fluorescent via the insertion of a fluorescent nucleobase, for example a fluorescent guanine-analog, into an oligonucleotide capable of forming a G-quadruplex structure resembling a telomeric repeat sequence. In some preferred embodiments, the telomeric repeat sequence is a human telomeric repeat sequence. The signal generated by this intrinsically fluorescent nucleobase-substituted quadruplex-DNA forming oligonucleotide sequence is extremely sensitive to the binding of a ligand, and thereby facilitates an effective, rapid means of screening hundreds of potential DNA-quadruplex ligands (or drugs of interest), irrespective of whether these ligands are, themselves, fluorescent. Notably, formation of the quadruplex structure is not affected; because the nucleobase analog is intrinsic to the G-quadruplex, cytotoxicity resulting from the interaction of the ligand with duplex DNA structures is not observed. Thus, the present invention provides methods for identifying potential DNA-quadruplex-binding molecules individually, and from libraries of compounds that may act as telomerase inhibitors, by their ability to stabilize formation of the G-quadruplex.

In some embodiments, the present invention provides methods for determining the binding affinity of a candidate compound for G-quadruplex structures comprising the steps of:
(a) providing a G-quadruplex analog, said analog having at least one intrinsic fluorescent moiety;
(b) contacting said G-quadruplex analog with a candidate compound; and
(c) measuring a difference in a fluorescence property of said G-quadruplex analog.

As used herein, the term "candidate compound" is intended to mean a compound, preferably a small molecule (i.e., a molecule having a molecular weight of less than 1000 daltons), that is suspected of possessing the ability to bind to G-quadruplex structures. Examples of such compounds are molecules having multiple aromatic, heteroaromatic, alicyclic and heterocyclic ring systems.

As used herein, the term "G-quadruplex analog" is intended to mean a polynucleotide analog in accordance with the present invention that forms a G-quadruplex structure, and which preferably contains an intrinsic fluorescent moiety.

As used herein, the term "intrinsic fluorescent moiety" is intended to mean a fluorescent moiety that is an intrinsic part of the G-quadruplex analog, i.e., a moiety that is a fluorophore, and that is substituted for constituent part of a G-quadruplex-forming polynucleotide, as opposed to a fluorophore that is appended to a nucleobase, sugar or internucleosidic linkage of a polynucleotide through a tether. Thus, an example of a preferred intrinsic fluorescent moiety is a fluorescent nucleobase that has been substituted for a nucleobase of a G-quadruplex-forming polynucleotide.

As used herein, the term "contacting" is intended to mean the placing together of the indicated moieties such that a binding reaction can occur.

As used herein, the term "fluorescent nucleobase analog" is intended to mean a nucleobase analog that is fluorescent. It is preferred that the fluorescent nucleobase not disrupt the G-quadruplex structure. However, while it is preferred that the fluorescent nucleobase analog participate in nucleobase pairing, such participation is not required. Thus, any of the numerous fluorescent nucleobase analogs known in the art to be useful in duplex or triplex structures can be used in the G-quadruplex analogs of the invention. Examples of such fluorescent nucleobases include 2-amino purine, and pteridine derivatives. On particularly preferred fluorescent nucleobase is 6-methyl-8-(2-deoxy-β-D-ribofuranosyl) isoxanthopterin ("6MI"), commercially available form TRI-LINK, San Diego, Calif. Examples of further fluorescent nucleobases will be apparent to those of skill in the art.

In accordance with the present invention, individual candidate compounds or libraries of candidate compounds are contacted with a G-quadruplex analog under conditions such that binding of the candidate compounds to the G-quadruplex analog can occur. In some embodiments, the degree of binding is determined by measuring a difference in a fluorescence property of said G-quadruplex analog; i.e., by measuring a difference in a fluorescence property of the intrinsic fluorescence moiety of the G-quadruplex analog. Any fluorescence property of the fluorescent moiety that changes in response to binding of a candidate compound can be used to determine the binding of the candidate compound to the G-quadruplex analog. Examples of such fluorescence properties include the emission wavelength, excitation wavelength, intensity, anisotropy, FRET and lifetime of the fluorescent moiety.

The G-quadruplex analogs of the invention possess at least one intrinsic fluorescent moiety, which is preferably a fluorescent nucleobase analog. In some embodiments, the G-quadruplex analogs contain one, two, three, four, five, six or more intrinsic fluorescent moieties.

In accordance with the present invention, the G-quadruplex analogs can form G-quadruplex structures. In some embodiments, the nucleobase sequence of the G-quadruplex analog is a telomeric repeat sequence. In some preferred embodiments, the nucleobase sequence of the G-quadruplex analog has a high degree of homology (for example, greater than 80% or greater than 90% homology) with a human telomeric repeat sequence. In some preferred embodiments, the nucleobase sequence of the G-quadruplex analog is identical, or is substantially identical to a telomeric repeat sequence (preferably but not necessarily a human telomeric sequence). In some embodiments, the G-quadruplex analog can contain a telomeric repeat sequence, or a sequence substantially identical thereto (for example a sequence identical to a telomeric repeat sequence but for the substitution of one or more fluorescent nucleobase analogs therein) and additional nucleobases. In some embodiments, the nucleobase sequence of the G-quadruplex analog is identical to a telomeric repeat sequence but for the substitution of one or more fluorescent nucleobase analogs therein. In some embodiments, the G-quadruplex analogs of the invention contain one, two, three, four, five or six fluorescent nucleobase analogs.

In some embodiments, the present invention provides G-quadruplex analog polynucleotides having the structure:

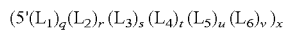

wherein:

each $L_1$, $L_2$, $L_3$, $L_4$, $L_5$ and $L_6$ is independently selected from the group consisting of a nucleotide, a nucleotide analog, and a nucleotide comprising a fluorescent nucleobase analog;

q, r, s, t, u and v are each independently 0, 1 or 2, provided that the sum of q+r+s+t+u+v is at least 3; and x is 1 to 8;

provided that:

said sequence 5'-$(L_1)_q(L_2)_r(L_3)_s(L_4)_t(L_5)_u(L_6)_v$ is an analog of a telomeric repeat sequence;

said polynucleotide contains at least one nucleotide comprising a fluorescent nucleobase analog; and said polynucleotide is a G-quadruplex analog.

As used herein, the term "nucleotide" has its accustomed meaning of a monomeric unit of DNA or RNA. See L. Stryer, Biochemistry 4$^{th}$ edition, W.H Freeman and Co., N.Y. 1995, incorporated herein by reference. The term "nucleotide analog" as used herein is intended to mean a moiety that mimics the structure and/or function of naturally occurring nucleotide, typically a nucleotide in which one of the constituent moieties (i.e., the sugar, the internucleoside linkage, or particularly the nucleobase) has been modified or substituted by a different moiety. Myriad nucleotide analogs are known in the art. See for example Antisense Research and Application, Ed. S. T. Crooke and B. Lebleu, CRC Press, 1993, incorporated by reference herein.

In some preferred embodiments, the G-quadruplex analogs have the structure of any of SEQ ID NOs: 1-16, and wherein at least one of said nucleobases of said SEQ ID NOs: 1-16 has been replaced with a fluorescent nucleobase analog. In further preferred embodiments, the G-quadruplex analog has the structure of any of SEQ ID NOs: 1-16 and one or more guanine bases of positions G5 and G11 have been replaced with a fluorescent nucleobase analog. In some particularly preferred embodiments, the guanine base of position G5 has been replaced with a fluorescent nucleobase analog; or the guanine base of position G11 has been replaced with a fluorescent nucleobase analog; or the guanine bases of positions G5 and G11 have been replaced with a fluorescent nucleobase analog.

In accordance with some preferred embodiments of the invention, large numbers of candidate compounds (e.g., libraries) can be screened to identify compounds that bind G-quadruplex structures. Such compounds are believed to possess telomerase inhibitory activity. In some embodiments, the telomerase inhibitory activity of such identified compounds is determined by telomerase assays known in the art.

In some embodiments, candidate compounds are contacted with an array of G-quadruplex analogs of the invention. Such an array can be in any of the numerous forms routinely used for high throughput screening. Examples of such arrays are 96-well plates, high density arrays on substrates (e.g., so-called "gene chips"; see for example U.S. Pat. Nos. 5,445,934 and 5,520,270, both to Fodor, and both incorporated by reference herein), and other types of screening methodologies known in the art.

In some embodiments, the G-quadruplex analogs have the structure of any of SEQ ID NOs: 2-8 and 10-16, and wherein at least one of said nucleobases of said SEQ ID NOs: 2-8 and 10-16 has been replaced with a fluorescent nucleobase analog. In further embodiments, the G-quadruplex analogs have the structure of any of SEQ ID NOs: 1-8 and one or more guanine bases of positions G5 and G11 have been replaced with a fluorescent nucleobase analog. In some preferred embodiments, the G-quadruplex analogs have the structure of any of SEQ ID NOs: 1-8 and the guanine base of position G5 has been replaced with a fluorescent nucleobase analog, or the guanine base of position G11 has been replaced with a fluorescent nucleobase analog, or the guanine bases of positions G5 and G11 have been replaced with a fluorescent nucleobase analog.

In some embodiments, the present invention provides methods for identifying a candidate compound as a telomerase inhibitor comprising the steps of:

(a) providing a G-quadruplex analog, said analog having at least one intrinsic fluorescent moiety;

(b) contacting said G-quadruplex analog with said candidate compound; and (c) measuring a difference in a fluorescence property of said G-quadruplex analog upon binding of said compound to said analog. Optionally, the candidate compounds identified as having G-quadruplex binding properties can then be assayed for telomerase inhibitory activity by any of the variety of telomerase activity assays known in the art.

Synthesis of polynucleotides of the invention can be accomplished by standard methodologies, for example phosphoramidite methodologies. See for example Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069, each of which is incorporated by reference. See also *Oligonucleotides and Analogues A Practical Approach*, Eckstein, F. Ed., IRL Press, New York, 1991, also incorporated by reference in its entirety.

The G-quadruplex analogs of the invention can contain, in addition to the intrinsic fluorescent moiety, any of a wide variety of known oligonucleotide modifications, including base modifications, backbone modifications, phosphate modifications, sugar modifications, and 2' modifications. Thus, the G-quadruplex structure can contain, for example, modified internucleoside linkages such as phosphodiester, phosphorothioate, phosphorodithioate, and H-phosphonate linkages, naturally occurring pentose sugar components such as ribose and deoxyribose, and their substituted derivatives, as well as other sugars known to substitute therefor in oligonucleotide analogs.

The constituent sugars and nucleosidic bases of the G-quadruplex structures of the invention can be naturally occurring or non-naturally occurring. Non-naturally occurring sugars and nucleosidic bases are typically structurally distinguishable from, yet functionally interchangeable with, naturally occurring sugars (e.g. ribose and deoxyribose) and nucleosidic bases (e.g., adenine, guanine, cytosine, thymine). Thus, non-naturally occurring nucleobases and sugars include all such structures which mimic the structure and/or function of naturally occurring species, as is known in the art.

As discussed above, the G-quadruplex analogs of the invention, for example pteridine substituted quadruplex forming DNA polynucleotides described herein, demonstrate a decrease in fluorescence intensity on binding with ligands. In accordance with some aspects of the present invention, this parameter is quantified and used in the fast and sensitive binding assays described herein.

The present invention provides several advantages over prior assays. For example, the methods of the present invention facilitate the screening of large libraries of candidate compounds for G-quadruplex stabilization. Successful candidates can then be assayed independently for telomerase inhibition. Due to the high fluorescence quantum yield of the substituted sequences of the invention, (preferably but not necessarily the G5 and/or G11 substituted sequences described herein), the assay can be performed using nanomolar quadruplex concentrations in a suitable array format, for example a "DNA chip" or a 96-well plate, which can be read very quickly using a well known methodologies, for example, a fluorescence plate reader. The assay methods of the invention are discussed herein using 96-well plates as an example of such methodology. However, it will be appreciated that any of the known screening methodologies can be used in accordance with the methods described herein. In some particularly preferred embodiments, the assay methods of the invention are performed on high density arrays ("gene chips") as are known in the art.

In one embodiment of the assays of the invention, potential quadruplex-stabilizing molecules are added individually to arrays (e.g., the wells of 96-well plates) and incubated. The time of incubation can easily be determined by routine stop-flow measurements. Typically, controls are used in the performance of the assays of the invention.

Because binding in the assays of the present invention is determined using the intrinsic fluorescence of the G-quadruplex structure, the disadvantages of the prior assays described above are eliminated. In addition, the assays of the invention are much more readily performed using large scale screening techniques, as described above.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Materials and Methods:

Oligonucleotides DNA and Porphyrins:

Human telomeric sequence (TTAGGG) 4 (SEQ ID NO: 4) was purchased from Oligos etc, (HPLC purified).ss-DNA (polyA), ds-DNA {poly (dA)-poly (dT)}, triplex DNA {poly (dA)-[poly (dT)2]} were purchased from Amersham Inc. Fluorescently labeled guanine-telomeric 24-mer sequences 5tet (TTAGGGTTAG$\underline{F}$GTTAGGGTTAGGG) (SEQ ID NO: 17)and 11 tet (TTAGGGTTAGGGTTAGGGTTAG$\underline{F}$G) (SEQ ID NO: 18)were provided by Dr. Mary Hawkins (NIH/Maryland). Quadruplex were formed by heating the DNA at 90 C. for 10 minutes then cooling slowly to room temperature in a buffer containing 100 mM KCL and 10 mM Cacodylate. Porphyrins were purchased from Porphyrin products (Logan, Utah) and were used with no further purification.

Fluorescence Measurements:

Fluorescence titrations were performed on a Spex Fluorolog instrument. All fluorescence measurements were carried out in buffer solution containing 10 mM sodium cacodylate and 100 mM KCl. Excitation was set at 340 nm and fluorescence emission was set at 430 nm for 6MI G-quadruplex analogs.

Fluorescence Studies:

Binding of 6MI G-quadruplex analogs of the invention to candidate compounds was determined through measurement of changes in fluorescence intensity. These 6MI analogs were found to display relatively little movement not associated with the motion of the DNA. In the case of conventionally attached probes, flexibility of linker arms allows movement of the flourophore in ways that are independent of the movement of the DNA being studied. This level of independent motion leads to more complex results. Because of this native-like linkage to DNA, these probes are very closely associated with neighboring bases rendering them exquisitely sensitive to subtle changes that occur in the DNA structure surrounding them. Changing in base stacking of base pairing in the vicinity of these probes is reflected by distinct changes in fluorescence properties of the pteridine. This sensitivity to neighboring base is not duplicated by conventional linker-attached probes which are more removed from these interactions by the length of the carbon chain connecting them to the DNA. Probes which are differ to nucleosides in size or structure can not be linked to the DNA through a deoxyribose moiety without a linker because they would most likely to disrupt the DNA tertiary structure and therefore not allow native-like interactions.

Pteridine nucleoside analogs have the advantage of that they are quenched when incorporated into an oligonucleotides (sometimes referred to as self-quenching). This feature can be used in many ways to monitor changing in tertiary structure occurring within the DNA as the bases interact with other molecules.

The pteridine analog 6MI was used as probes to investigate the interaction between G-quadruplex DNA and porphyrin. The pteridine analogs have the advantage of that they are highly fluorescent and both 3MI and 6MI have structural similarity to guanines (especially 6MI, which is known to be involved in base pairing and expected to form G-quadruplex structures). Also, their fluorescence properties such as excitation and emission maxima differ from that of native DNA and porphyrins.

G-Quadruplex Formation:

The effect of incorporating pteridine nucleoside analog (6MI) on quadruplex formation was examined by following the melting temperature of the sequence containing the probe at different position, the melting temperature measurement concluded that the incorporation of 6MI as DNA probe has no effect on quadruplex formation; this was demonstrated by recording the melting temperature at 295 nm. The telomeric sequence containing the probe showed high melting temperature (55° C.) similar to that of telomeric sequence without the 6MI probe. Also, the G-quadruplex formation was examined by gel electrophoresis (DNA shadowing) as the sequence containing the probe run as two separate bands (one as single-stranded DNA and the other is quadruplex DNA), especially, in presence of KCl which is known to stabilize G-quadruplex structures.

Incorporation of 6MI in position G5 formed more stable quadruplex structures compared to incorporating the same probe in the G11 position, as shown by gel electrophoresis and the higher melting temperature of the sequence containing 6MI in G5 position. While not wishing to be bound by any particular theory, it is believed that 6MI cannot form a bond with the guanine bases that is as strong as the guanine-guanine Hoogsteen base pairing. Thus, the G-quadruplex structure will have a free 3'-end when the G11 is substituted by 6MI, while substitution at G5 will be more stable as the G11 can form Guanine-guanine base pairing. This observation was confirmed by monitoring the quenching of the 6MI probe due to the quadruplex structure formation by increasing the KCl concentration to 100 mM and monitoring the fluorescence intensity, sequence with the probe at G5 position showed higher degree of quenching compared to the incorporation of 6MI in G11 position. This high degree of quenching is believed to be due to decrease in distance between the bases and the 6MI probe due to quadruplex formation.

Figure 3:
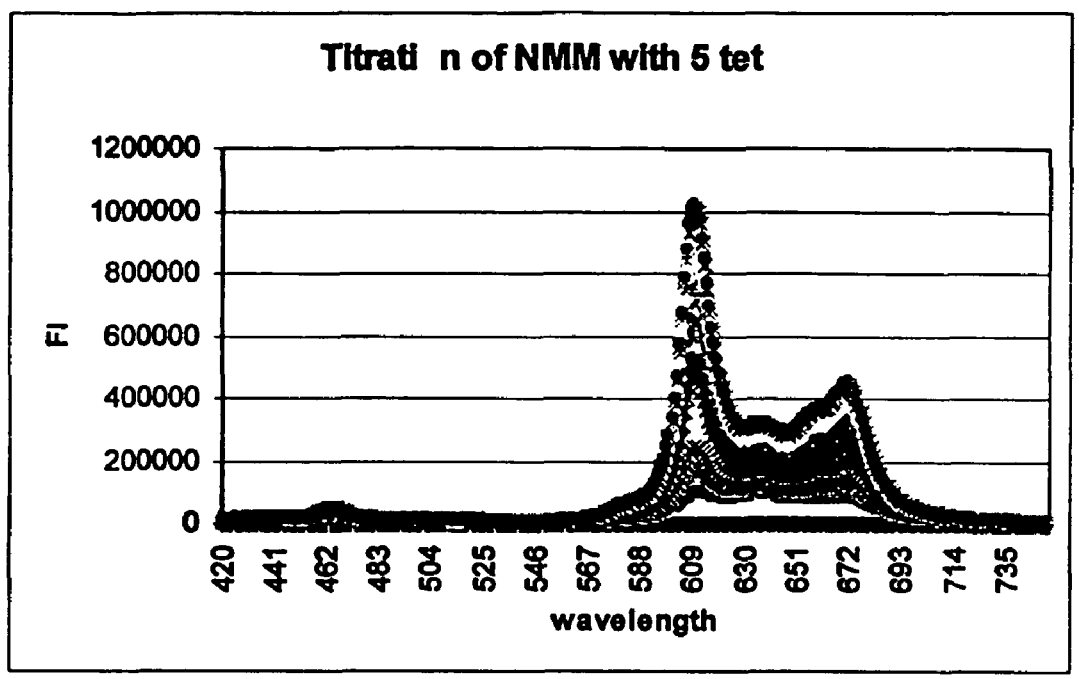
FIG. 3 shows the increase in intrinsic fluorescence intensity of NMM as the concentration of DNA telomeric sequence increases, with measurements carried out in 10 mM cacodylate and 100 mM potassium chloride buffer, and excitation of 410 nm, and emission at 610 nm.

In addition to gel electrophoresis and melting temperature experiments, the ability of pteridine analogs to form quadruplex DNA was examined using NMM titration study. It was found that the fluorescence intensity of NMM increases dramatically as the concentration of telomeric sequence with pteridine analogs at different position (tet5 and tet11) increase. This increase in fluorescence intensity confirmed that the presence of pteridine analogs incorporated into DNA sequence have no effect on quadruplex formation (FIG. 3).

A particular advantage of the methods of the invention is that the candidate compound need not possess any fluorescence properties. By following the decrease in fluorescence intensity of the G-quadruplex analog, one can determine the binding affinity and selectivity of a ligand to DNA.

Figure 4:
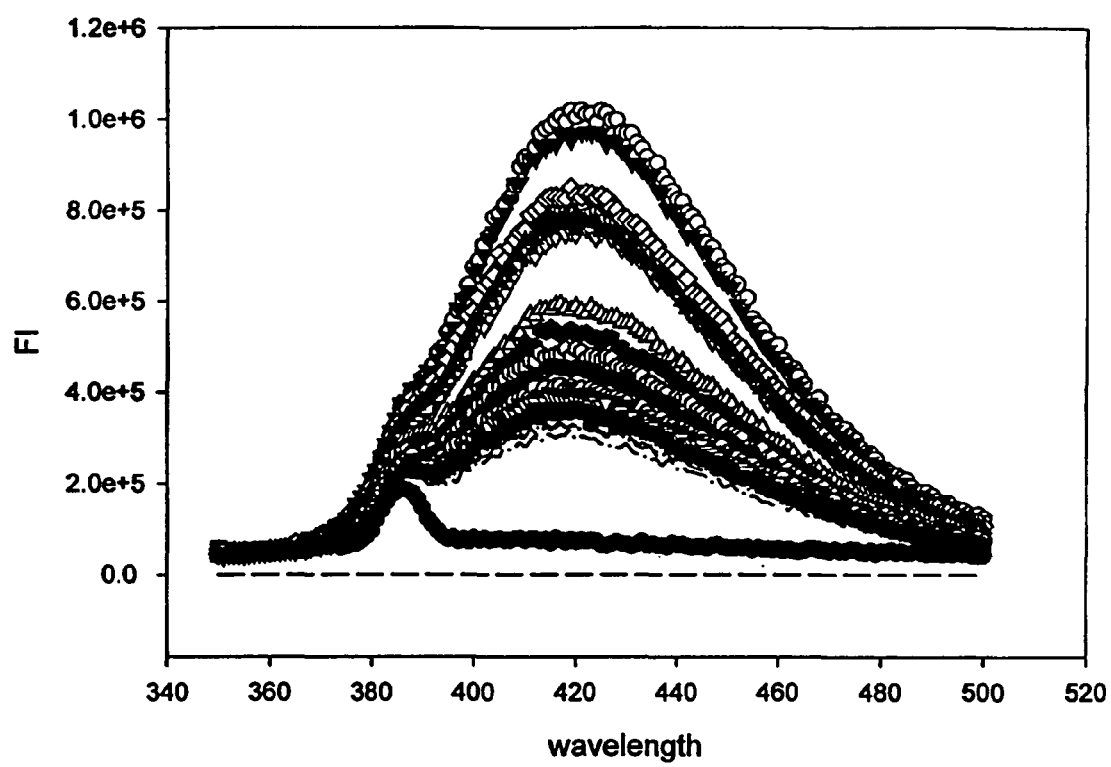
FIG. 4 shows the titration of fluorescent telomeric sequence (5 tet) with TMPy, with measurements were carried out in 10 mM cacodylate buffer, and monitoring of the decrease in fluorescence intensity of the 5 tet after the addition of TMPy in μM range, where excitation was at 340 nm and emission was recorded at 430 nm.

6MI was incorporated at different positions of a human telomeric sequence. specifically, G5 and G11 were replaced by 6MI to form tet5 and tet11 respectively), and the interaction of fluorescent porphyrins (FIG. 4) as well as non-fluorescent porphyrins were investigated. An increase of NMM concentration results in drop in fluorescence intensity of tet5.

Figure 5:
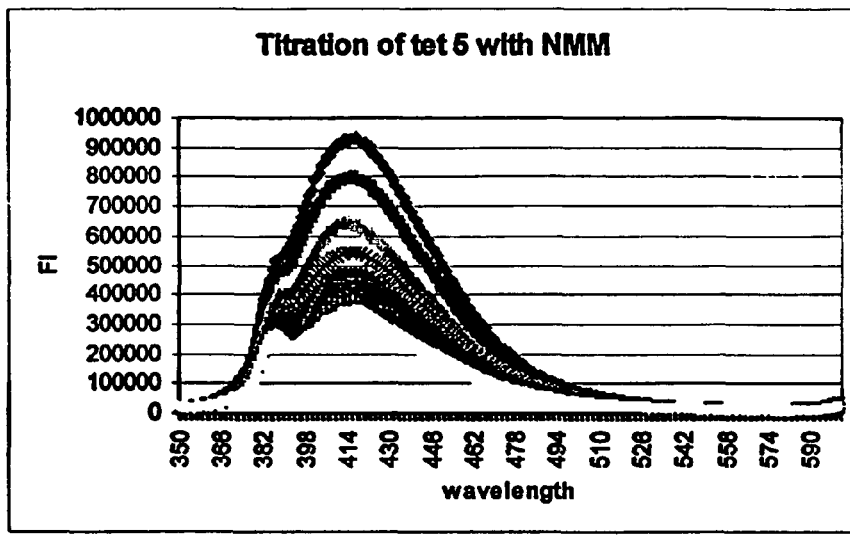
FIG. 5 shows the decrease in fluorescence intensity of 5 tet as the concentration of NMM increases, with excitation set at 340 nm and emission set at 430 nm.

The decrease in fluorescence intensity of pteridine analogs for both tet 5 and tet 11 was monitored as the concentration of NMM was increased (FIG. 5), and our results showed that NMM bind to both sequences with a slightly preference to tet 5 which have shown to be more stable than tet 11 as noticed from melting temperature and gel electrophoresis experiments.

Figure 6:
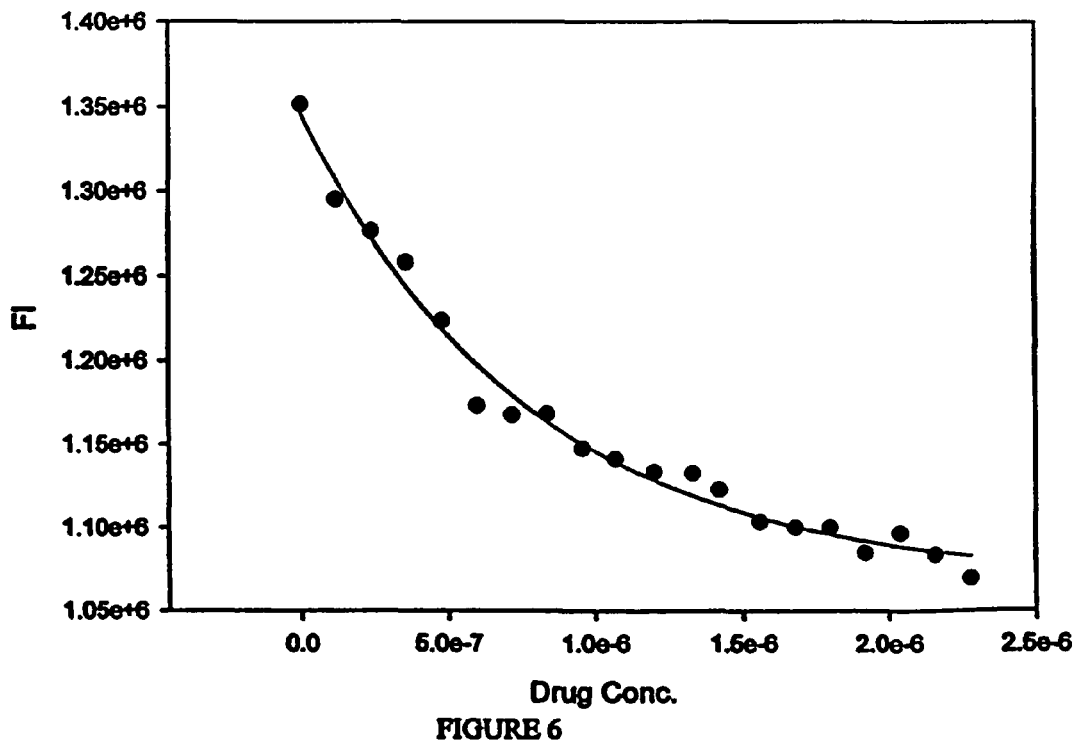
FIG. 6 shows the decrease in fluorescence of tet with the increase in Co(III)MPIX concentration.

Co(MPIX) is an example of non-fluorescent porphyrin. UV data have shown that Co(MPIX) is an excellent candidate for telomerase inhibition as shown by high quadruplex stabilization effect and relatively high affinity and high selectivity. Binding of Co(MPIX) to quadruplex DNA by fluorescence technique was carried out by using telomeric sequence with 6MI probe in position G5, by following the decrease in fluorescence intensity of pteridine analogs as the concentration of the drug was increased (FIG. 6). The binding constant of Co(MPIX) to quadruplex DNA was found to be higher ($10^7$) than that of NMM to the same telomeric sequence ($10^6$). These results were in agreement with the UV studies. Porphyrins such as Co (III) MPIX and NMM which possess a high specificity for quadruplex over duplex DNA and relatively high binding affinity are predicted to be ideal agents for use in therapeutic approaches aimed to inhibit telomerase activity and thus inhibit the growth of cancer cells.

The reference works, patents, patent applications, and scientific literature, and other printed publications that are mentioned of referred to herein are hereby incorporated by reference in their entirety. In addition, the following references are also incorporated herein by reference in their entirety:

Anantha, N. V., Azam, M., & Sheardy, R. D. (1998) *Biochemistry* 37, 2709-2714.

Arthanari, H., Basu, S., Kawano, T. L., & Bolton, P. H. (1998) *Nucleic Acids Research* 26, 3724-728.

Bare, L. A., Trinh, L., Wu, S., & Devlin, J. J. (1998) *Drug Devlopment Research* 43, 109-116.

Davies, A. J. & Siu, L. L. (2000) *Cancer Investigation* 18, 269-277.

Elmore, L. W. & Holt, S. E. (2000) *Molecular Carcinogenesis* 28,

Fedoroff, O. Yu., Salazar, M., Han, H., Chemeris, V. V., Kerwin, S. M., & Hurley, L. H. (1998) *Biochemistry* 37, 12367-12374.

Han, H., Hurley, L. H., & Salazar, M. (1999) *Nucleic Acids Research* 27, 537-542.

Haq, I. L. J. E., Chowdhry, B. Z., & Jenkins, T. C. (1996) *Journal of the American Chemical Society* 118, 10693-10701.

Hemann, M. T. & Greider, C. W. (1999) *Nucleic Acids Research* 27, 3964-3969.

Herbert, B.-S., Pitts, A. E., Baker, S. I., Hamilton, S. E., Wright, W. E., Shay, J. W., & Corey, D. R. (1999) *PNAS* 96, 14276-14281.

Hurley, L. H., Wheelhouse, R. T., Sun, D., Kerwin, S. M., Salazar, M., Fedoroff, Yu. O., Han, F. X., Han, H., Izbicka, E., & Von Hoff, D. D. (2000) *Pharmacology and Therapeutics* 85, 141-158.

Li, Y., Geyer, R., & Sen, D. (1996) *Biochemistry* 35, 6911-6922.

Mergny, J.-L., Phan, A.-T., & Lacroix, L. (1998) *FEBS Letters* 435, 74-78.

Neidler, S., Harrison, R. J., Reszka, A. P., & Read, M. A. (2000) *Pharmacology and Therapeutics* 85, 133-139.

Perry, P. J. & Jenkins, T. C. (1999) *Exp. Opin. Invest. Drugs* 8, 1981-2008.

Voloshchuk, N., Hawkins, M., and Davenport, L. (2000) *Biophysical J.,* 78, 30.

Voloshchuk, N., Hawkins, M., and Davenport, L. (2001) *Biophysical J.,* 80, 294a.

As those skilled in the art will appreciate, numerous changes and modifications may be made to the preferred embodiments of the invention without departing from the spirit of the invention. It is intended that all such variations fall within the scope of the invention.

What is claimed is:

1. A G-quadruplex analog polynucleotide comprising the structure:

$$(5'\text{-}(L_1)_q(L_2)_r(L_3)_s(L_4)_t(L_5)_u(L_6)_v)_x$$

wherein:
- each $L_1$, $L_2$, $L_3$, $L_4$, $L_5$ and $L_6$ is independently selected from the group consisting of a nucleotide, a nucleotide analog, and a nucleotide comprising a 6-methyl-isoxanthopterin nucleobase;
- q, r, s, t, u and v are each independently 0, 1 or 2, provided that the sum of q+r+s+t+u+v is at least 3; and
- x is 1 to 8;

provided that:
- $5'\text{-}(L_1)_q(L_2)_r(L_3)_s(L_4)_t(L_5)_u(L_6)_v$ is a analog of a telomeric repeat sequence;
- said polynucleotide contains at least one nucleotide comprising a 6-methyl-isoxanthopterin nucleobase;
- said G-quadruplex analog polynucleotide forms a G-quadruplex structure; and
- wherein each 6-methyl-isoxanthopterin nucleobase is located within said G-quadruplex structure.

2. The G-quadruplex analog polynucleotide of claim 1 wherein the G-quadruplex analog polynucleotide is an analog of a human telomeric repeat sequence.

3. The G-quadruplex analog polynucleotide of claim 1 wherein q, r, s, t, u and v are each 1.

4. The G-quadruplex analog polynucleotide of claim 3 wherein x is from 2 to 6.

5. The G-quadruplex analog polynucleotide of claim 3 wherein x is from 3 to 5.

6. The G-quadruplex analog polynucleotide of claim 3 wherein x is 4.

7. The G-quadruplex analog polynucleotide of claim 6 wherein said G-quadruplex analog polynucleotide contains one nucleotide comprising a 6-methyl-isoxanthopterin nucleobase.

8. The G-quadruplex analog polynucleotide of claim 6 wherein said G-quadruplex analog polynucleotide contains two nucleotides comprising a 6-methyl-isoxanthopterin nucleobase.

9. The G-quadruplex analog polynucleotide of claim 6 wherein said G-quadruplex analog polynucleotide contains three nucleotides comprising a 6-methyl-isoxanthopterin nucleobase.

10. The G-quadruplex analog polynucleotide of claim 6 wherein said G-quadruplex analog polynucleotide contains four nucleotides comprising a 6-methyl-isoxanthopterin nucleobase.

11. The G-quadruplex analog polynucleotide of claim 6 wherein said G-quadruplex analog polynucleotide contains five nucleotides comprising a 6-methyl-isoxanthopterin nucleobase.

12. The G-quadruplex analog polynucleotide of claim 6 wherein said G-quadruplex analog polynucleotide contains six nucleotides comprising a 6-methyl-isoxanthopterin nucleobase.

13. A compound comprising of any of SEQ ID NOs: 1-8 wherein at least one G nucleobase therein has been replaced with a 6-methyl-isoxanthopterin nucleobase, provided that said compound forms a G-quadruplex structure; and wherein each 6-methyl-isoxanthopterin nucleobase is located within said G-quadruplex structure.

14. The compound of claim 13 wherein the compound comprises any of SEQ ID NOs: 2-8.

15. The compound of claim 13 wherein the compound comprises any of SEQ ID NOs: 3-5.

16. The compound of claim 13 wherein the compound comprises SEQ ID NO: 4.

17. An array comprising the G-quadruplex analog polynucleotide of claim 1.

18. An array comprising the G-quadruplex analog polynucleotide of claim 2.

19. An array comprising the G-quadruplex analog poloynucleotide of claim 3.

20. A G-quadruplex analog polynucleotide comprising:
- a nucleobase sequence that is an analog of a telomeric repeat sequence; and
- at least one nucleotide comprising a 6-methyl-isoxanthopterin nucleobase;

wherein:
- said G-quadruplex analog polynucleotide forms a G-quadruplex; and
- each 6-methyl-isoxanthopterin nucleobase is located within said G-quadruplex structure.

* * * * *

SEQUENCE LISTING

```
<160> NUMBER OF SEQ ID NOS: 16

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 1 ttaggg                                                              6

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 2
ttagggttag gg                                                      12

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 3
ttagggttag ggttaggg                                                18

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 4
ttagggttag ggttagggtt aggg                                         24

<210> SEQ ID NO 5
<211> LENGTH: 30
<212> TYPE: DNA
<213> ORGANISM: Artificial Sequence
<220> FEATURE:
```

```
<223> OTHER INFORMATION: Description of Artificial Sequence:
      G-quadruplex

<400> SEQUENCE: 5
ttagggttag ggttagggtt agggttaggg                                    30

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 6
ttagggttag ggttagggtt agggttaggg ttaggg                             36

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 7
ttagggttag ggttagggtt agggttaggg ttagggttag gg                      42

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 8
ttagggttag ggttagggtt agggttaggg ttagggttag ggttaggg                48

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 9 attggg                                                               6

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 10
attgggattg gg                                                       12

<210> SEQ ID NO 11
<211> LENGTH: 18
<212> TYPE: DNA
<213> ORGANISM: Artificial Sequence
```

```
<220> FEATURE:
<223> OTHER INFORMATION: Description of Artificial Sequence:
      G-quadruplex

<400> SEQUENCE: 11
attgggattg ggattggg                                                    18

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 12
attgggattg ggattgggat tggg                                             24

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 13
attgggattg ggattgggat tgggattggg                                       30

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 14
attgggattg ggattgggat tgggattggg attggg                                36

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 15
attgggattg ggattgggat tgggattggg attgggattg gg                         42

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence:
      G-quadruplex

<400> SEQUENCE: 16
attgggattg ggattgggat tgggattggg attgggattg ggattggg                   48
```